(12) United States Patent
Li et al.

(10) Patent No.: US 10,788,446 B1
(45) Date of Patent: Sep. 29, 2020

(54) ION-SENSITIVE FIELD-EFFECT TRANSISTOR WITH MICRO-PILLAR WELL TO ENHANCE SENSITIVITY

(71) Applicant: International Business Machines Corporation, Armonk, NY (US)

(72) Inventors: Juntao Li, Cohoes, NY (US); Kangguo Cheng, Schenectady, NY (US); Ruilong Xie, Niskayuna, NY (US); Chanro Park, Clifton Park, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/378,844

(22) Filed: Apr. 9, 2019

(51) Int. Cl.
| | | |
|---|---|---|
| *G01N 27/414* | (2006.01) | |
| *H01L 29/51* | (2006.01) | |
| *H01L 21/311* | (2006.01) | |
| *H01L 29/423* | (2006.01) | |

(Continued)

(52) U.S. Cl.
CPC ....... *G01N 27/414* (2013.01); *H01L 21/0337* (2013.01); *H01L 21/31116* (2013.01); *H01L 21/31144* (2013.01); *H01L 21/32051* (2013.01); *H01L 27/092* (2013.01); *H01L 29/423* (2013.01); *H01L 29/513* (2013.01); *H01L 29/518* (2013.01); *B81B 2201/0214* (2013.01);

(Continued)

(58) Field of Classification Search
CPC . H01L 2924/13072; H01L 2924/13073; H01L 29/513; H01L 29/518; H01L 41/1132; G01N 27/414; G01N 27/4141; G01N 27/4143; G01N 27/4145; G01N 27/4146; G01N 27/4148; G01N 33/54373; G01N 33/5438; B81B 2201/0214; B81B 2203/0361; B81C 1/00206

See application file for complete search history.

(56) References Cited

U.S. PATENT DOCUMENTS

| | | |
|---|---|---|
| 7,211,459 B2 | 5/2007 | Yang |
| 7,321,143 B2 | 1/2008 | Kunath et al. |

(Continued)

FOREIGN PATENT DOCUMENTS

| | | |
|---|---|---|
| CN | 106501340 A | 3/2017 |
| WO | 2016085126 A1 | 6/2016 |

OTHER PUBLICATIONS

Hajmirzaheydarali et al., "Ultrahigh Sensitivity DNA Detection Using Nanorods Incorporated ISFETs", IEEE Electron Device Letters, 2016, pp. 663-666, vol. 37, Issue 5.

*Primary Examiner* — Jose R Diaz
(74) *Attorney, Agent, or Firm* — Vazken Alexanian; Ryan, Mason & Lewis, LLP

(57) ABSTRACT

A semiconductor device includes a first passivation layer disposed on a semiconductor base. The semiconductor device further includes a dielectric layer disposed on the first passivation layer. The semiconductor device further includes a plurality of pillars disposed in an opening in the dielectric layer and the first passivation layer and from a top surface of the semiconductor base. The semiconductor device further includes a metal layer disposed on the exterior surfaces of the plurality of pillars and sidewalls of the dielectric layer and the first passivation layer and on the exposed top surface of the semiconductor base. The semiconductor device further includes a second passivation layer disposed on the metal layer and a top surface of the semiconductor device; wherein the second passivation layer has an electrical charge.

8 Claims, 20 Drawing Sheets

(51) Int. Cl.
  *H01L 27/092* (2006.01)
  *H01L 21/3205* (2006.01)
  *H01L 21/033* (2006.01)
  *B81C 1/00* (2006.01)
  *G01N 33/543* (2006.01)
(52) U.S. Cl.
  CPC ... *B81B 2203/0361* (2013.01); *B81C 1/00206* (2013.01); *G01N 33/5438* (2013.01); *G01N 33/54373* (2013.01); *H01L 2924/13072* (2013.01); *H01L 2924/13073* (2013.01)

(56) References Cited

U.S. PATENT DOCUMENTS

| | | |
|---|---|---|
| 8,642,371 B2 | 2/2014 | Mohajerzadeh et al. |
| 8,758,688 B2 | 6/2014 | De Keersmaecker et al. |
| 8,821,798 B2 | 9/2014 | Bustillo et al. |
| 8,936,763 B2 | 1/2015 | Rothberg et al. |
| 9,171,873 B2 * | 10/2015 | Luo .................. H01L 21/02568 |
| 9,606,079 B2 * | 3/2017 | Merz ........................ G01N 27/26 |
| 9,746,442 B2 | 8/2017 | Hekmatshoartabari et al. |
| 9,960,253 B2 | 5/2018 | Fife |
| 9,968,927 B2 * | 5/2018 | Liu .................... G01N 21/6454 |
| 2010/0273672 A1 * | 10/2010 | Demoustier-Champagne ............ G01N 33/54373 506/9 |
| 2017/0059517 A1 * | 3/2017 | Bustillo ............ H01L 29/42324 |
| 2017/0131267 A1 | 5/2017 | Lee et al. |
| 2018/0070869 A1 * | 3/2018 | Ionescu ................ A61B 5/4266 |
| 2018/0366340 A1 | 12/2018 | Waggoner et al. |
| 2019/0011424 A1 | 1/2019 | McRuer et al. |
| 2019/0128838 A1 * | 5/2019 | Cheng .................... H01L 29/518 |
| 2020/0041447 A1 * | 2/2020 | Chang ................ G01N 27/4148 |

* cited by examiner

ION-SENSITIVE FIELD-EFFECT TRANSISTOR WITH MICRO-PILLAR WELL TO ENHANCE SENSITIVITY

BACKGROUND

Biological and chemical sensors based on ion-sensitive field effect transistors (ISFET) can be integrated with modern microelectronic devices and used to detect and measure various aspects of chemical reactions and substance properties. For example, an ISFET may be used to measure ion concentrations, such as hydrogen ion concentration, in a sample of an analyte. An ISFET is similar to a metal oxide semiconductor field effect transistor (MOSFET), but lacks a gate electrode. Instead, an ion-sensitive membrane is placed over the channel region of the ISFET and is exposed to the analyte sample. A reference electrode of the ISFET is separated from the ion-sensitive membrane by the solution. The potential difference between the channel and the reference electrode is a function of the ion concentration in the analyte sample. An operating characteristic of the ISFET may be measured and used to calculate ion concentration.

SUMMARY

Embodiments described herein provide methods of forming semiconductor devices. For example, one exemplary embodiment includes a method for fabricating a semiconductor device comprising depositing a first passivation layer on a semiconductor base. The method further comprises depositing a dielectric layer on the first passivation layer. The method further comprises depositing a hardmask on the dielectric layer. The method further comprises patterning and etching an opening into the hardmask, the dielectric layer and the first passivation layer which exposes a top surface of the semiconductor base and forms a plurality of pillars in the opening, wherein a top surface of the plurality of pillars is below a top surface of the hardmask on the dielectric layer defining a width of the opening. The method further comprises depositing a metal layer on the exterior surfaces of the dielectric layer, the plurality of pillars and the exposed top surface of the semiconductor base in the opening and over the top surface of the hardmask on the dielectric layer defining the width of the opening. The method further comprises depositing a sacrificial layer in the opening. The method further comprises removing the exposed metal layer disposed on the top surface of the hardmask on the dielectric layer. The method further comprises depositing a second passivation layer on the metal layer and the top surface of the hardmask on the dielectric layer. The method further comprises forming an electrical charge in the second passivation layer.

Another exemplary embodiment includes a method for fabricating a semiconductor device comprising depositing a first passivation layer on a semiconductor base. The method further comprises depositing a first dielectric layer on the first passivation layer. The method further comprises etching an opening into the first dielectric layer and the first passivation layer which exposes a top surface of the semiconductor base. The method further comprises forming a second dielectric layer on each sidewall of the first dielectric layer and the first passivation layer in the opening. The method further comprises forming a third dielectric layer on each sidewall of the second dielectric layer defining an opening therebetween. The method further comprises depositing a fourth dielectric layer in the opening between the third dielectric layer on each sidewall of the second dielectric layer. The method further comprises recessing a top surface of the second dielectric layer, the third dielectric layer and the fourth dielectric layer to below a top surface of the first dielectric layer. The method further comprises removing the second dielectric layer and the fourth dielectric layer which exposes a top surface of the semiconductor base and forms an opening. The method further comprises depositing a metal layer on the exterior surfaces of the first dielectric layer, the third dielectric layer and the exposed top surface of the semiconductor base in the opening and over the top surface of the first dielectric layer defining the width of the opening. The method further comprises depositing a sacrificial layer in the opening. The method further comprises removing the metal layer disposed on the top surface of the first dielectric layer. The method further comprises depositing a second passivation layer on the metal layer and the top surface of the first dielectric layer. The method further comprises forming an electrical charge in the second passivation layer.

Another exemplary embodiment includes a semiconductor device comprising a first passivation layer disposed on a semiconductor base. The semiconductor device further comprises a dielectric layer disposed on the first passivation layer. The semiconductor device further comprises a plurality of pillars disposed in an opening in the dielectric layer and the first passivation layer and from a top surface of the semiconductor base. The semiconductor device further comprises a metal layer disposed on the exterior surfaces of the plurality of pillars and sidewalls of the dielectric layer and the first passivation layer and on the exposed top surface of the semiconductor base. The semiconductor device further comprises a second passivation layer disposed on the metal layer and a top surface of the semiconductor structure; wherein the second passivation layer has an electrical charge.

These and other features, objects and advantages of the present invention will become apparent from the following detailed description of illustrative embodiments thereof, which is to be read in connection with the accompanying drawings.

DETAILED DESCRIPTION

Figure 1:
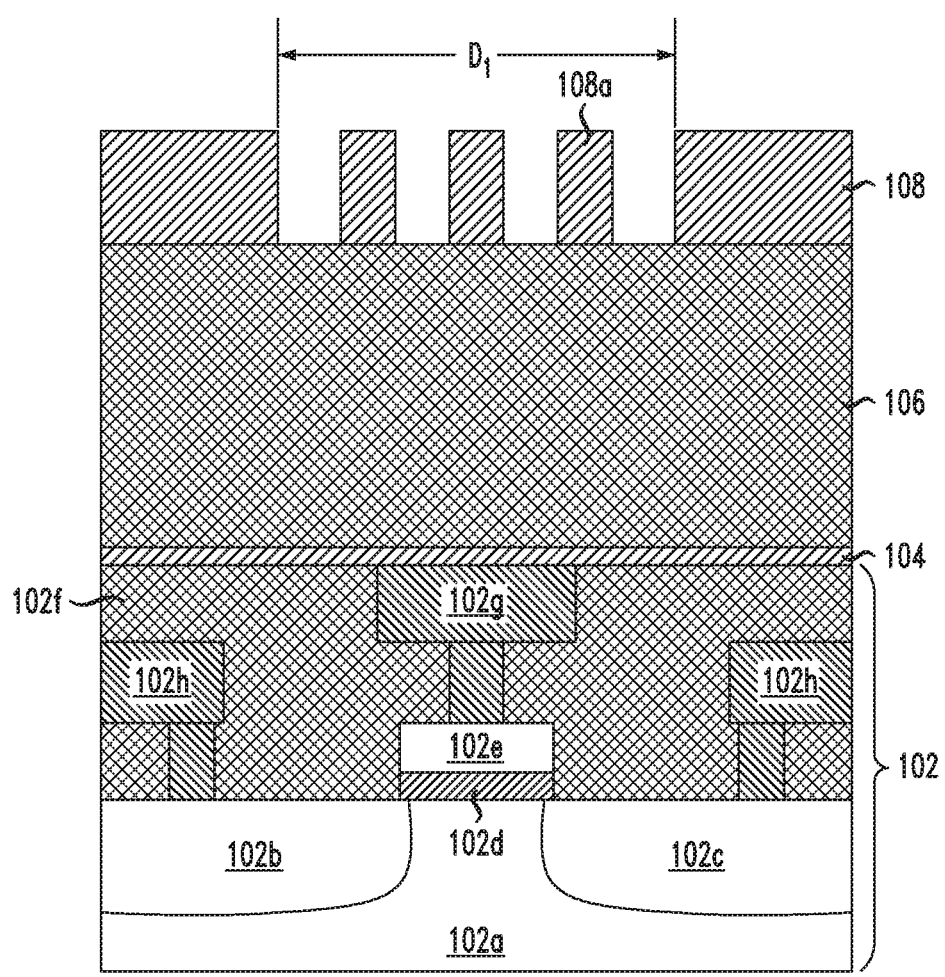
FIG. 1 is a schematic cross-sectional view of a semiconductor structure at a first-intermediate fabrication stage, in accordance with an illustrative embodiment.

The present invention generally relates to semiconductor manufacturing and, more particularly, to device structures, fabrication methods, and design structures for a biological or chemical sensor.

As stated above, biological and chemical sensors can be based on an ISFET (i.e., transistor). In general, an ISFET can be fabricated along with standard MOSFET to make a "lab-on-chip" in which ISFETs are used as sensors and MOSFETs are used for signal processing. A passivation layer (e.g., silicon nitride) is typically used on top of the last metal layer of the MOSFET. The passivation layer serves two purposes: (1) it prevents ions such as sodium or potassium from getting into the underlying transistor, and (2) it serves as a sensing layer to absorb electric charges from an analyte solution into the surface of the passivation layer. The amount of electrical charges is measured by the threshold voltage change of the underlying transistor, thus analyte (biological or chemical) in a micro-well is sensed.

However, a passivation layer reduces the sensitivity of the underlying ISFET because it creates a capacitance ($C_p$) in series with the FET capacitance ($C_{FET}$). Compared with the case without a passivation layer (analyte directly contacting the gate), the sensitivity of the ISFET is reduced to a factor of A, where A can be expressed as:

$$A = C_p/(C_p + C_{FET}).$$

The passivation layer is typically much thicker than the gate dielectric layer. Therefore, $C_p$ is much less than $C_{FET}$.

As a result, A is much less than 1. Therefore, there is a need to improve the sensitivity of ISFET.

Accordingly, enhanced sensitivity of an ISFET according to the present invention can increase the passivation capacitance due to an increase of surface area by forming vertical standing micro-pillars inside a micro well.

It is to be understood that the various layers, structures, and regions shown in the accompanying drawings are schematic illustrations that are not drawn to scale. In addition, for ease of explanation, one or more layers, structures, and regions of a type commonly used to form semiconductor devices or structures may not be explicitly shown in a given drawing. This does not imply that any layers, structures, and regions not explicitly shown are omitted from the actual semiconductor structures.

Furthermore, it is to be understood that the embodiments discussed herein are not limited to the particular materials, features, and processing steps shown and described herein. In particular, with respect to semiconductor processing steps, it is to be emphasized that the descriptions provided herein are not intended to encompass all of the processing steps that may be required to form a functional semiconductor integrated circuit device. Rather, certain processing steps that are commonly used in forming semiconductor devices, such as, for example, wet cleaning and annealing steps, are purposefully not described herein for economy of description.

Moreover, the same or similar reference numbers are used throughout the drawings to denote the same or similar features, elements, or structures, and thus, a detailed explanation of the same or similar features, elements, or structures will not be repeated for each of the drawings. It is to be understood that the terms "about" or "substantially" as used herein with regard to thicknesses, widths, percentages, ranges, etc., are meant to denote being close or approximate to, but not exactly. For example, the term "about" or "substantially" as used herein implies that a small margin of error may be present, such as 1% or less than the stated amount.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment. The term "positioned on" means that a first element, such as a first structure, is present on a second element, such as a second structure, wherein intervening elements, such as an interface structure, e.g. interface layer, may be present between the first element and the second element.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present concept.

As used herein, "height" refers to a vertical size of an element (e.g., a layer, trench, hole, opening, etc.) in the cross-sectional views measured from a bottom surface to a top surface of the element, and/or measured with respect to a surface on which the element is located. Conversely, a "depth" refers to a vertical size of an element (e.g., a layer, trench, hole, opening, etc.) in the cross-sectional views measured from a top surface to a bottom surface of the element. Terms such as "thick", "thickness", "thin" or derivatives thereof may be used in place of "height" where indicated.

As used herein, "width" or "length" refers to a size of an element (e.g., a layer, trench, hole, opening, etc.) in the drawings measured from a side surface to an opposite surface of the element. Terms such as "thick", "thickness", "thin" or derivatives thereof may be used in place of "width" or "length" where indicated.

As used herein, terms such as "upper", "lower", "right", "left", "vertical", "horizontal", "top", "bottom", and derivatives thereof shall relate to the disclosed structures and methods, as oriented in the drawing figures. For example, as used herein, "vertical" refers to a direction perpendicular to the top surface of the substrate in the cross-sectional views, and "horizontal" refers to a direction parallel to the top surface of the substrate in the cross-sectional views.

As used herein, unless otherwise specified, terms such as "on", "overlying", "atop", "on top", "positioned on" or "positioned atop" mean that a first element is present on a second element, wherein intervening elements may be present between the first element and the second element. As used herein, unless otherwise specified, the term "directly" used in connection with the terms "on", "overlying", "atop", "on top", "positioned on" or "positioned atop" or the term "direct contact" mean that a first element and a second element are connected without any intervening elements, such as, for example, intermediary conducting, insulating or semiconductor layers, present between the first element and the second element.

One illustrative embodiment for forming an ISFET will be described below with reference to FIGS. 1-8. Note that the same reference numeral (100) is used to denote the semiconductor structure through the various intermediate fabrication stages illustrated in FIGS. 1 through 8. Note also that the ISFET described herein can also be considered to be a semiconductor device and/or an integrated circuit, or some part thereof. FIG. 1 illustrates a cross sectional view of an ISFET at a first-intermediate fabrication stage. For the purpose of clarity, several fabrication steps leading up to the production of the ISFET as illustrated in FIG. 1 are omitted. In other words, the ISFET does not necessarily start out in the form illustrated in FIG. 1, but may develop into the illustrated structure over one or more well-known processing steps which are not illustrated but are well-known to those of ordinary skill in the art.

Referring to FIG. 1, a semiconductor structure 100 comprises a semiconductor base 102. In general, semiconductor base 102 can have semiconductor components (e.g., transistor, etc.) formed therein such as, by way of example, a complementary metal oxide semiconductor (CMOS) integrated circuit (IC) logic device which contains both n-type field effect transistors (NFETs) and p-type field effect transistors (PFETs). For example, semiconductor base 102 can be formed by standard CMOS flow including implementing a gate over the semiconductor fins. In addition, semiconductor base 102 can include a substrate 102a, source 102b and a drain 102c, a gate oxide 102d and metal gate 102e contacted to a BEOL metal 102g, together with metal contacts 102h in a dielectric layer 102f. For clarity, the semiconductor structure discussed herein will reference the semiconductor base as semiconductor base 102 or semiconductor base 202 or semiconductor base 302.

Semiconductor structure 100 further includes a passivation layer 104 disposed on a top surface of semiconductor base 102. Passivation layer 104 includes, for example, silicon nitride and may be formed by any conventional deposition process such as chemical vapor deposition (CVD), physical vapor deposition (PVD), plasma enhanced chemical vapor deposition (PECVD), atomic layer deposition (ALD), chemical solution deposition or other like processes. The thickness of passivation layer 104 can be relatively thin, e.g., a thickness ranging from about 3 nanometers (nm) to about 6 nm. More specifically, the passivation layer 104 can have a thickness of, e.g., about 5 nm.

Semiconductor structure 100 further includes a dielectric layer 106 disposed on a top surface of passivation layer 104. Suitable dielectric material for dielectric layer 106 includes, for example, silicon nitride, silicon oxide, silicon dioxide, silicon oxynitride, a dielectric metal oxide, a dielectric metal nitride, or a combination thereof. The dielectric layer 106 may be formed by suitable deposition processes, for example, CVD, PVD, PECVD, ALD, chemical solution deposition or other like processes. The thickness of the dielectric material may vary depending on the deposition process as well as the composition and dielectric material used.

Semiconductor structure 100 further includes a hardmask 108 disposed over dielectric layer 106. For illustrative purposes of the present invention, hardmask 108 may be silicon dioxide ($SiO_2$) or silicon nitride ($Si_3N_4$), depending on the material for dielectric layer 106. In addition, a photoresist layer (not shown) may be provided above hardmask 108. In at least one embodiment of the present invention, hardmask 108 can be patterned or etched by any technique known in the art to form a pillar mask 108a in micro well region defined by $D_1$. For example, etching may be accomplished by etching into the substrate utilizing a conventional dry etching process such as reactive-ion etching (RIE) or plasma etching. RIE is a form of plasma etching in which during etching the surface to be etched is placed on a radio-frequency powered electrode. Moreover, during RIE the surface to be etched takes on a potential that accelerates the etching species extracted from plasma toward the surface, in which the chemical etching reaction is taking place in the direction normal to the surface. Other examples of anisotropic etching that can be used at this point of the present invention include ion beam etching, plasma etching or laser ablation.

Figure 2:
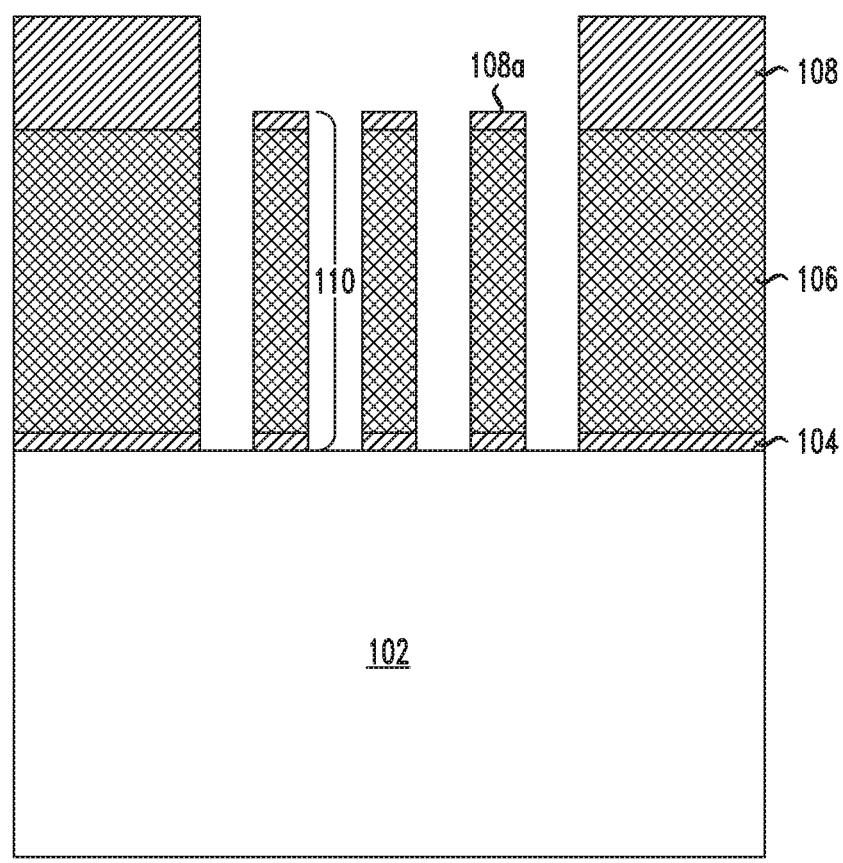
FIG. 2 is a schematic cross-sectional view of a semiconductor structure at a second-intermediate fabrication stage, in accordance with an illustrative embodiment.
Figure 3:
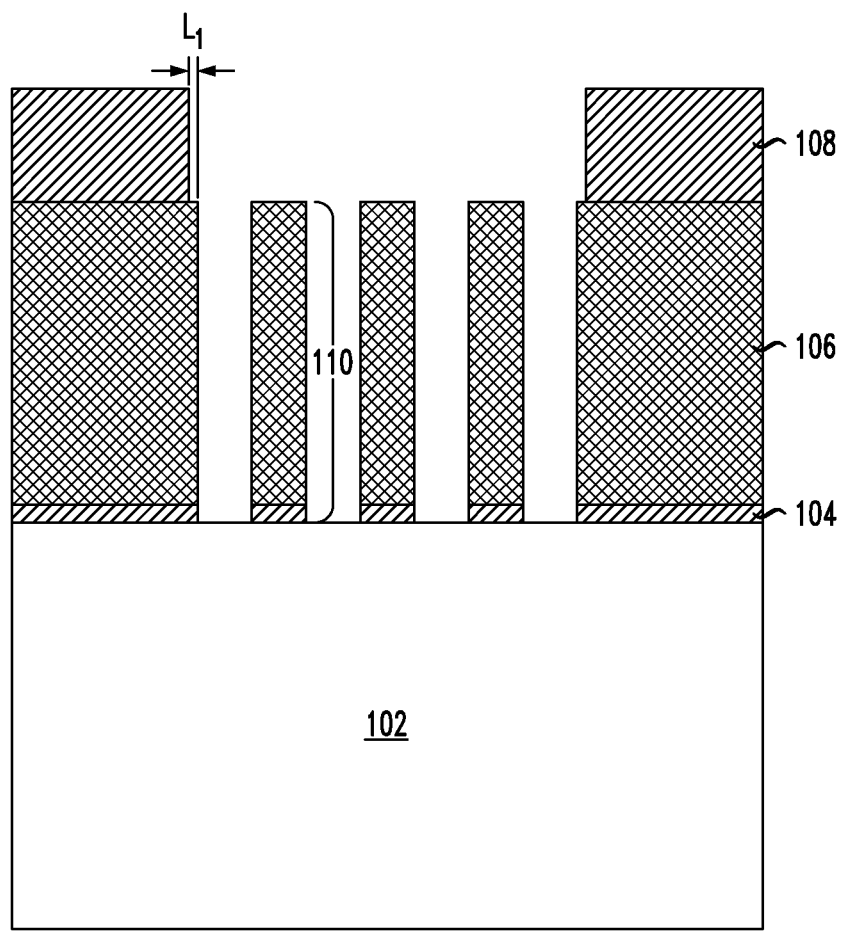
FIG. 3 is a schematic cross-sectional view of a semiconductor structure at a third-intermediate fabrication stage, according to an illustrative embodiment.

FIG. 2 illustrates a view of a semiconductor structure 100 at a second-intermediate fabrication stage. First, a directional etch technique such as, for example, RIE, is carried out through dielectric layer 106 that exposes the top surface of passivation layer 104 to form pillars 110. When carrying out this directional etch, a portion of hardmask 108 is removed from the top of pillars 110.

Next, the exposed passivation layer 104 is removed utilizing an isotropic etching process that selectivity removes the passivation layer 104 and exposes the top surface of semiconductor base 102. The isotropic etch may be a wet or dry etch that is selective to the material in passivation layer 104. If desired, an additional isotropic etch of hardmask 108 can be carried out to completely remove the hardmask 108 on top of pillars 110 while removing a portion of the top surface of hardmask 108 on dielectric layer 106, e.g., about 0.3 μm or less, and portion of sidewalls of hardmask 108 on dielectric layer 106 defined by $L_1$. See FIG. 3. The geometry of the pillars in the micro-well resulting from the selective etching of dielectric material can increase total capacitor surface area as compared to other designs. In addition, this can enhance the sensitivity of the underlying ISFET by increasing capacitor surface area as compared to other designs.

Figure 4:
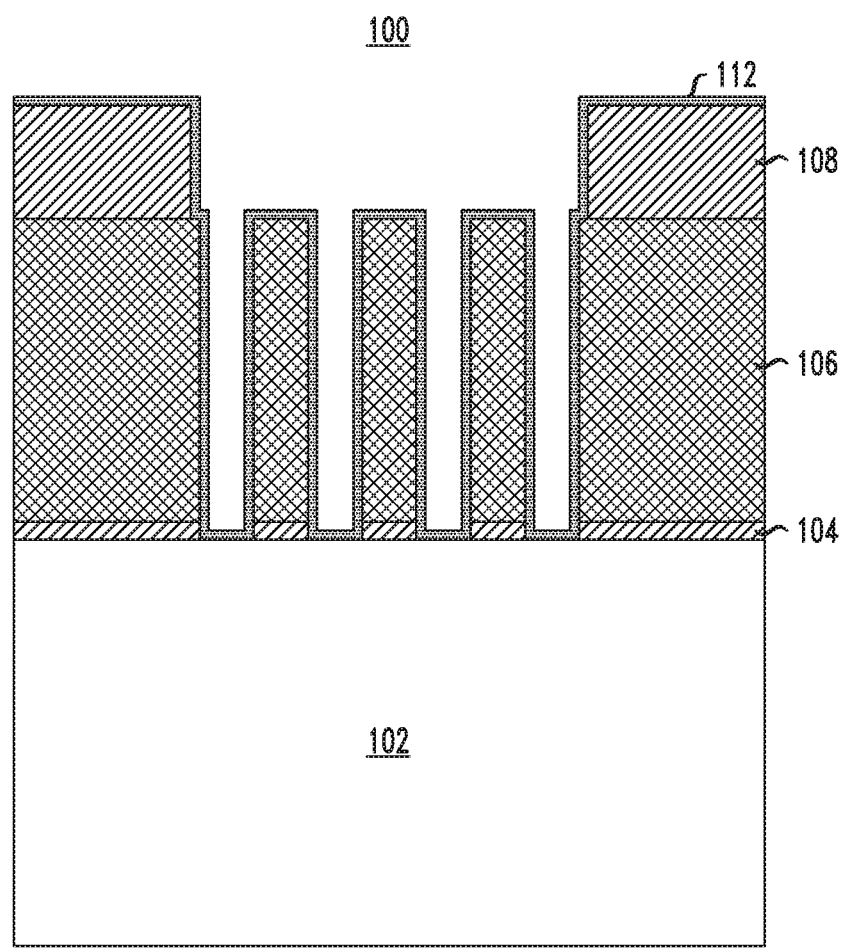
FIG. 4 is a schematic cross-sectional view of a semiconductor structure at a fourth-intermediate fabrication stage, according to an illustrative embodiment.

FIG. 4 illustrates a view of semiconductor structure 100 at a fourth-intermediate fabrication stage. During this stage metal layer 112 is deposited on the exposed surfaces of semiconductor base 102, passivation layer 104, dielectric layer 106, hardmask 108 and pillars 110. Suitable metallic material for metal layer 112 includes, for example, tungsten, titanium, tantalum, ruthenium, zirconium, cobalt, copper, aluminum, lead, platinum, tin, silver, and gold. Metal layer 112 can be formed by a suitable deposition process, for example, ALD.

Figure 5:
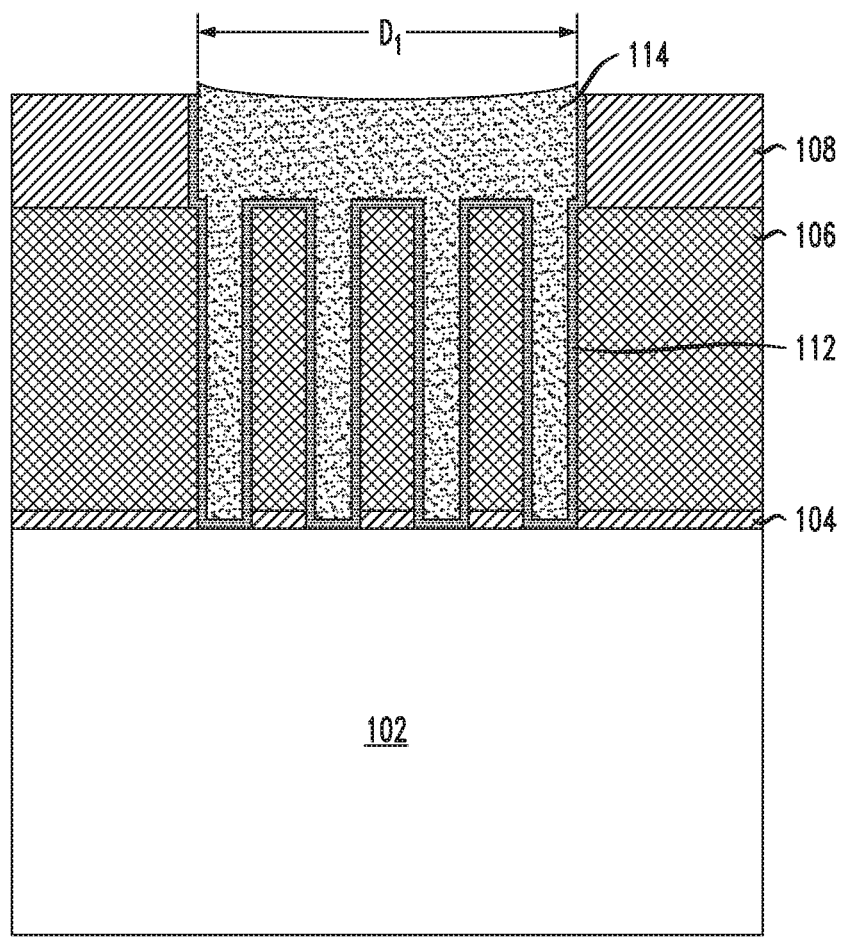
FIG. 5 is a schematic cross-sectional view of a semiconductor structure at a fifth-intermediate fabrication stage, according to an illustrative embodiment.

FIG. 5 illustrates a cross-sectional view of semiconductor structure 100 at a fifth-intermediate fabrication stage. During this stage, a sacrificial material 114 is deposited in the micro-well defined by $D_1$ and over the top surface of semiconductor structure 100 including metal layer 112 on the top surface of hardmask 108 (not shown). Suitable sacrificial material includes, for example, amorphous materials such as amorphous silicon, an amorphous silicon germanium alloy (aSiGe) and the like. Sacrificial material 114 can be deposited by any conventional deposition process such as CVD, PVD, PECVD, ALD, chemical solution deposition or other like processes. Sacrificial material 114 is then planarized by, for example, a planarization process such as a chemical mechanical planarization (CMP). Optionally, sacrificial material 114 can be recessed in the micro-well to remove the residual of sacrificial material 114 (if there is any) on top of the top surface of the metal 112 to expose the top surface of metal layer 112 on the top surface of hardmask 108. The exposed metal layer 112 on the top surface of hardmask 108 is removed utilizing an isotropic etching process that selectivity removes the metal layer 112 and exposes the top surface of hardmask 108. The isotropic etch may be a wet or dry etch that is selective to the metal layer 112.

Figure 6:
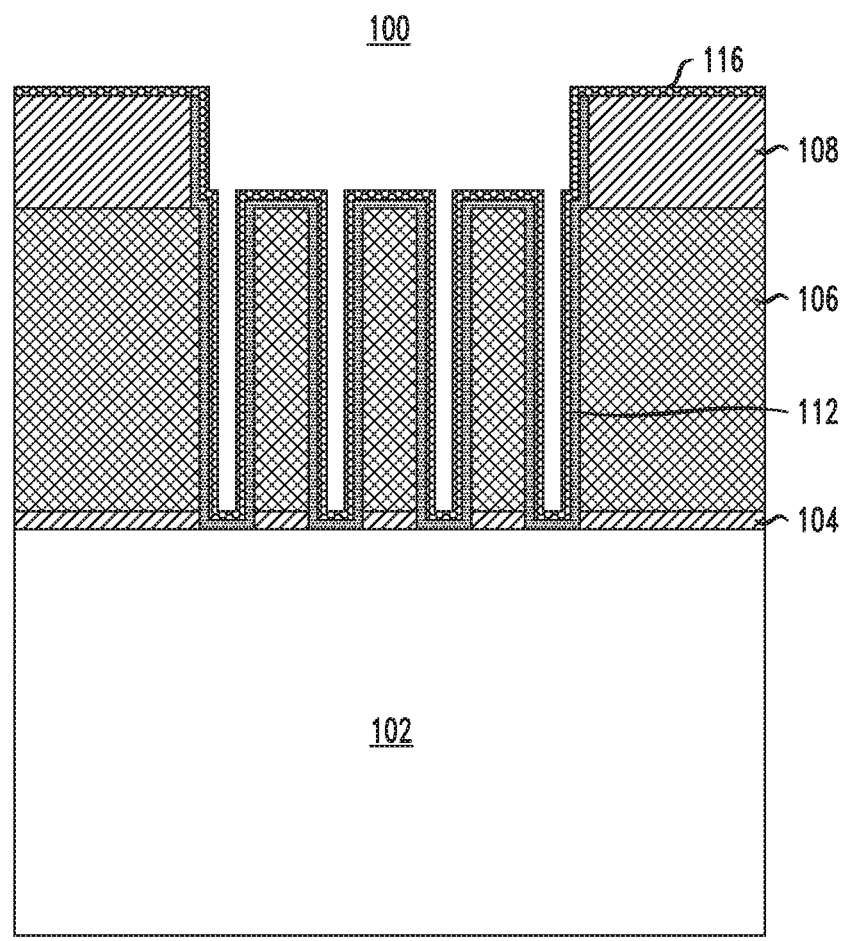
FIG. 6 is a schematic cross-sectional view of a semiconductor structure at a sixth-intermediate fabrication stage, according to an illustrative embodiment.

FIG. 6 illustrates a view of semiconductor structure 100 at a sixth-intermediate fabrication stage. During this stage, sacrificial material 114 is removed by conventional techniques, e.g., by a gas phase HCL etch, and passivation layer 116 is deposited on the exposed surfaces of hardmask 108 and metal layer 112. The passivation layer 116 can be used to, e.g., (1) prevent ions (e.g., sodium (Na) and/or potassium (K) ions) from getting into the underlying transistor, and (2) serve as a sensing layer to absorb electric charges in the analyte solution applied to the surface of the passivation layer 116. The passivation layer 116 can include any suitable material in accordance with the embodiments described herein. Suitable material for passivation layer 116 includes, for example, SiN, $Al_2O_3$, $Ta_2O_5$, and the like. Passivation layer 116 can be deposited by any conventional deposition process such as CVD, PVD, PECVD, ALD, chemical solution deposition or other like processes.

Figure 7:
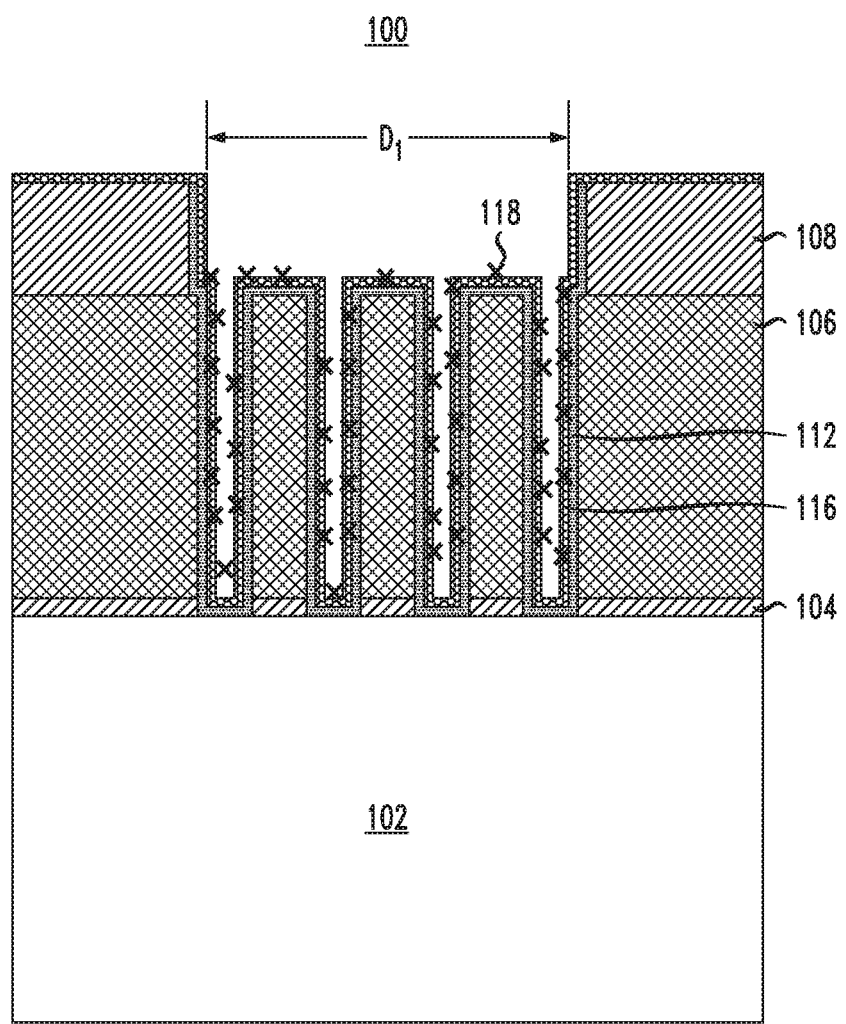
FIG. 7 is a schematic cross-sectional view of a semiconductor structure at a seventh-intermediate fabrication stage, according to an illustrative embodiment.

FIG. 7 illustrates a view of semiconductor structure 100 at a seventh-intermediate fabrication stage. FIG. 7 illustrates the exemplary structure of FIG. 6 after providing (i.e., introducing) an analyte-containing solution (not shown) to the micro-well. The term "analyte" is used throughout the present application to denote a substance (either chemical or biological), or a chemical or biological constituent that can be subject to analyses and detection by ISFET sensing. That is, the analyte is composed of a chemical or biological material that has, or can generate an electric charge 118, in a solution (aqueous or non-aqueous (polar or non-polar)) such that the amount of electrical charge 118 in the analyte-containing solution (not shown) can be measured by the threshold voltage change of the underlying FET. The resulting ISFET will have enhanced sensitivity by increasing the passivation capacitance due to increase of surface area by forming the vertical standing micro-pillars inside the micro well defined by $D_1$. For example, FIG. 8 illustrates a top down view of the micro-well of semiconductor structure 100 of FIG. 7 in accordance with the illustrative embodiment containing pillars 110 and the passivation layer with electrical charge 118.

Multiple vertical pillars are formed inside the micro-well and the geometry resulting from the selective etch process (e.g., vertical pillar-shaped geometry) can allow for an increased capacitor surface area as compared to other geometries (e.g., rectangular shaped geometries). As will be described in further detail below, sensitivity can be enhanced due to the increased capacitor surface area achieved by this geometry.

Although the passivation layer 116 can prevent ions from getting into the underlying transistor and can serve as a sensing layer to absorb electric charges in the analyte solution to the surface of the passivation layer 116, the passivation layer 116 can reduce the sensitivity of the underlying transistor. For example, the passivation layer 116 can create a passivation capacitance ($C_p$) in series with a FET capacitance ($C_{FET}$). More specifically, as compared with the case without a passivation layer (e.g., analyte directly contacting gate), the sensitivity of the underlying ISFET can be reduced by a factor of A, where A can be expressed as $A=C_p/(C_p+C_{FET})$. In the embodiment in which the passivation layer 116 has a thickness greater than that of the gate dielectric 102d in base 102, $C_p$ can be less than $C_{FET}$, thereby resulting in sensitivity value of A of less than 1. Based on this, the sensitivity of the underlying transistor can be increased by increasing the value of $C_p$. There is a direct relationship between total capacitor surface area and $C_p$, such that the greater the total capacitor surface area, the larger the capacitance value of $C_p$. Accordingly, increasing the total capacitor surface area can result in enhanced sensitivity of the underlying transistor.

Figure 8:
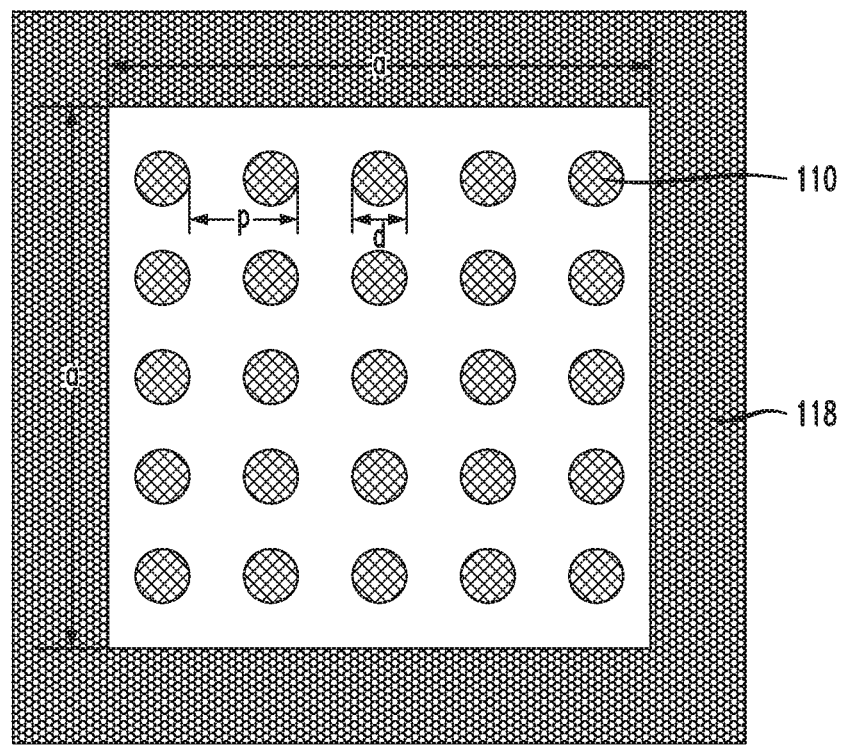
FIG. 8 is a top down view of the micro-well of the semiconductor structure of FIG. 7, in accordance with an illustrative embodiment.

For yet another example, vertical pillars with a smaller diameter "d" and pitch "P" as shown in FIG. 8 can be formed to achieve larger surface area and thus a higher passivation capacitance ($C_p$), which will result in further enhanced sensitivity of the underlying transistor.

Figure 9:
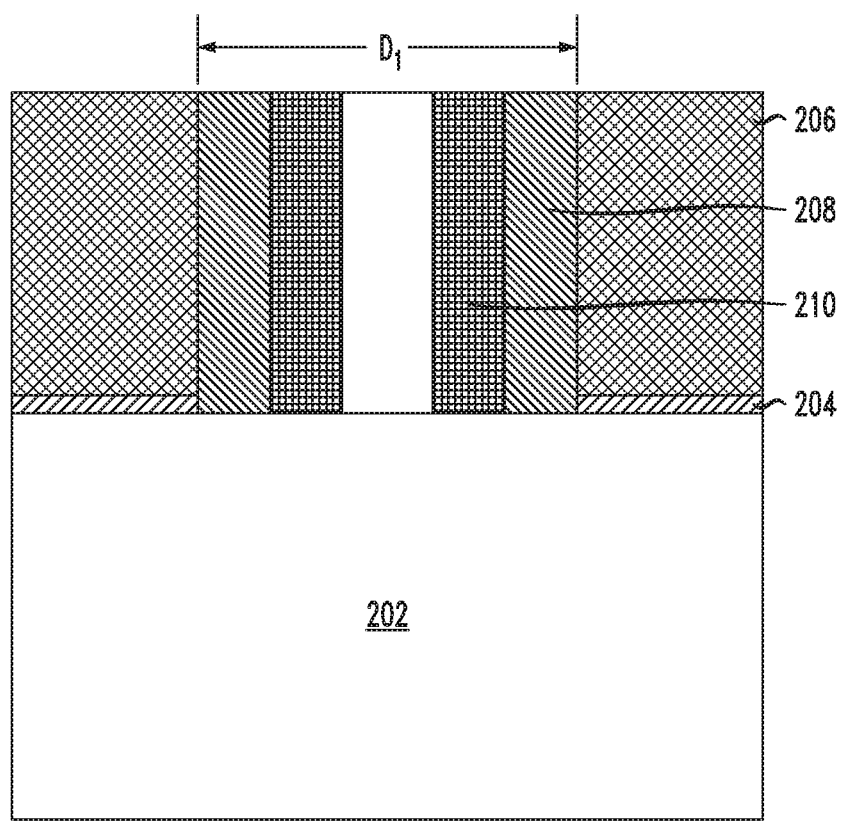
FIG. 9 is a schematic cross-sectional view of a semiconductor structure at a first-intermediate fabrication stage, according to another illustrative embodiment.

Another illustrative embodiment for forming an ISFET will be described below with reference to FIGS. 9-15. Note that the same reference numeral (200) is used to denote the semiconductor structure through the various intermediate fabrication stages illustrated in FIGS. 9 through 15. Note also that the ISFET described herein can also be considered to be a semiconductor device and/or an integrated circuit, or some part thereof. FIG. 9 illustrates a cross sectional view of an ISFET at a first-intermediate fabrication stage. For the purpose of clarity, several fabrication steps leading up to the production of the ISFET as illustrated in FIG. 9 are omitted. In other words, the ISFET does not necessarily start out in the form illustrated in FIG. 9, but may develop into the illustrated structure over one or more well-known processing steps which are not illustrated but are well-known to those of ordinary skill in the art.

Referring to FIG. 9, a semiconductor structure 200 comprises a semiconductor base 202. In general, semiconductor base 202 can be the same as described above for semiconductor base 102. Semiconductor structure 200 further includes a passivation layer 204 disposed on a top surface of semiconductor base 202 and a dielectric layer 206 disposed on a top surface of passivation layer 204. Passivation layer 204 and dielectric layer 206 can be the same as those described above for passivation layer 104 and dielectric layer 106. Micro-well defined as $D_1$ is formed by first depositing a hardmask (not shown) over the dielectric layer 206 as a mask to etch through the dielectric layer and exposing the top surface of passivation layer 204 layer, and then the hardmask is removed by conventional means. A first dielectric layer 208 (e.g., amorphous Si) is deposited on the top surface and sidewall of the dielectric layer 206 as well as the top surface of the passivation layer 204. A directional reactive ion etch is performed to remove the first dielectric layer 208 on the horizontal surfaces and form the first dielectric layer 208 as a first sidewall spacer. Then a second dielectric layer 210 (e.g., silicon nitride) is deposited. A directional reactive ion etch is then performed to remove the second dielectric layer 210 on the horizontal surfaces and form the second dielectric layer 210 as a second sidewall spacer. Next, the first dielectric layer 208 (such as a-Si) is deposited for the second time followed by a RIE etch process. The second dielectric layer 210 (such as SiN) is then deposited for the second time followed by the RIE process. This deposition/etch process can be repeated until the final gap is pinched off. As one skilled in the art will readily appreciate, depending on the thickness of the alternative layers and the dimension of the pre-defined micro well, multiple layer deposition and spacer RIE can be done before the final layer deposition pinches off.

Figure 10:
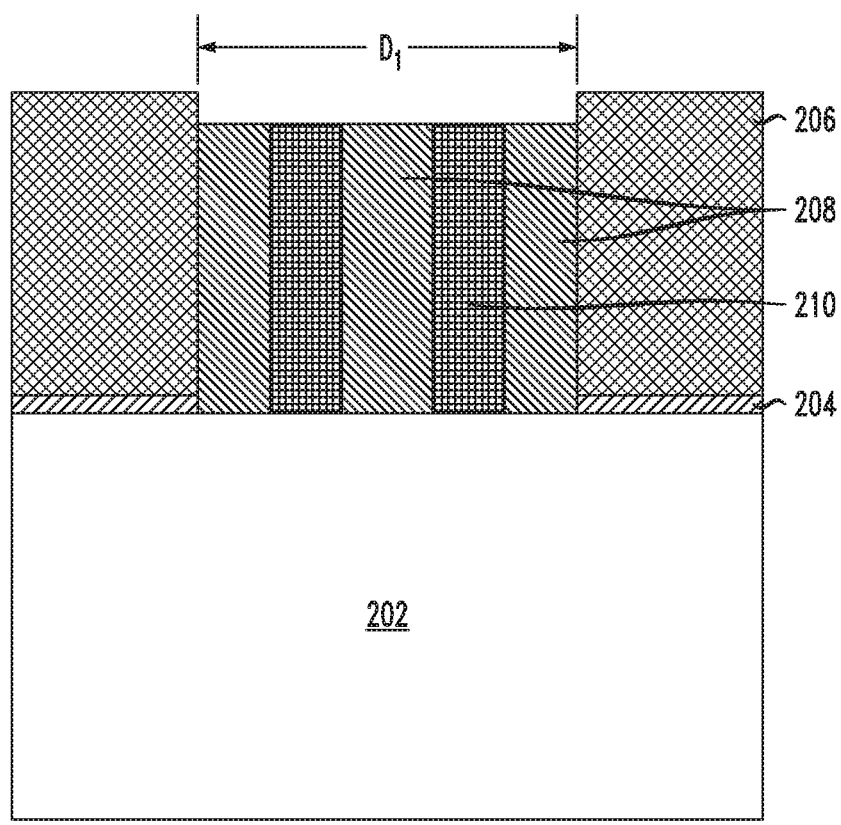
FIG. 10 is a schematic cross-sectional view of a semiconductor structure at a second-intermediate fabrication stage, according to another illustrative embodiment.

FIG. 10 illustrates a view of semiconductor structure 200 at a second-intermediate fabrication stage. During this stage, the top surface of the first dielectric layers 208, and second dielectric layers 210 is recessed to below a top surface of dielectric layer 206. The top surface of the first dielectric layers 208, and second dielectric layers 210 can be recessed using a selective directional removal technique that is selective to the first dielectric layers 208, and second dielectric layers 210, for example, a wet or dry isotropic etch.

Figure 11:
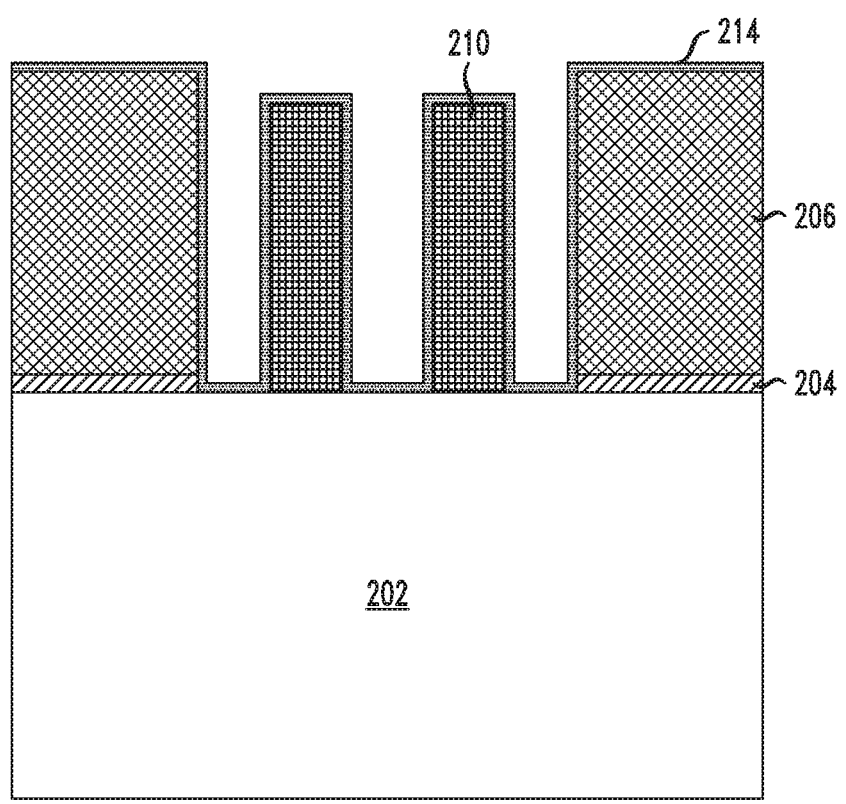
FIG. 11 is a schematic cross-sectional view of a semiconductor structure at a third-intermediate fabrication stage, according to another illustrative embodiment.

FIG. 11 illustrates a view of semiconductor structure 200 at a third-intermediate fabrication stage. During this stage, the first dielectric layers 208 are selectively removed utilizing an isotropic etching process that exposes the top surface of semiconductor base 202. The isotropic etch may be a wet or dry etch that is selective to the first dielectric layers 208. Next, metal layer 214 is deposited on the exposed surfaces of semiconductor base 202, dielectric layer 206, and second dielectric layers 210. Suitable metallic material and deposition techniques for metal layer 214 can be the same as those described above for metal layer 112.

Figure 12:
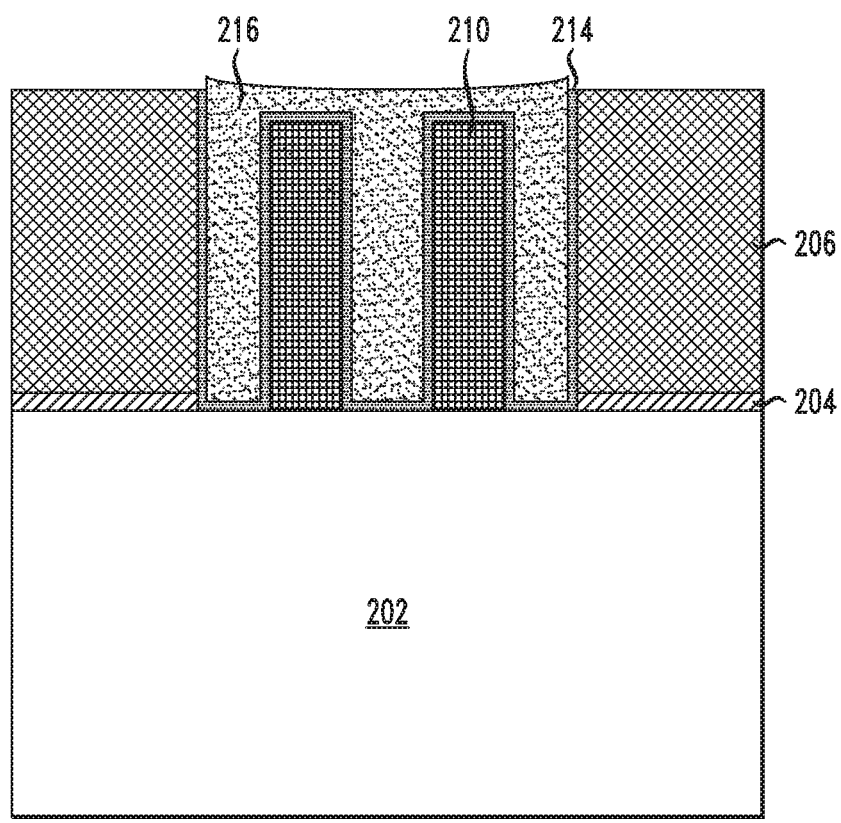
FIG. 12 is a schematic cross-sectional view of a semiconductor structure at a fourth-intermediate fabrication stage, according to another illustrative embodiment.

FIG. 12 illustrates a cross-sectional view of semiconductor structure 200 at a fourth-intermediate fabrication stage. During this stage, a sacrificial material 216 is deposited in the micro-well defined by $D_1$ and over the top surface of semiconductor structure 200 including metal layer 214 on the top surface of dielectric layer 206 (not shown). Suitable sacrificial material can be any of those described above for sacrificial material 114. Sacrificial material 216 can be deposited by any conventional deposition process such as CVD, PVD, PECVD, ALD, chemical solution deposition or other like processes. Sacrificial material 216 is then planarized by, for example, a planarization process such as CMP. Optionally, sacrificial material 216 can be recessed in the micro-well to remove the residual of sacrificial material 216 (if there is any) on top of the top surface of the metal 214 to expose the top surface of metal layer 214 on the top surface of dielectric layer 206 (not shown). The exposed metal layer 214 on the top surface of dielectric layer 206 is removed utilizing an isotropic etching process that selectivity removes the metal layer 214 and exposes the top surface of dielectric layer 206. The isotropic etch may be a wet or dry etch that is selective to the metal layer 214.

Figure 13:
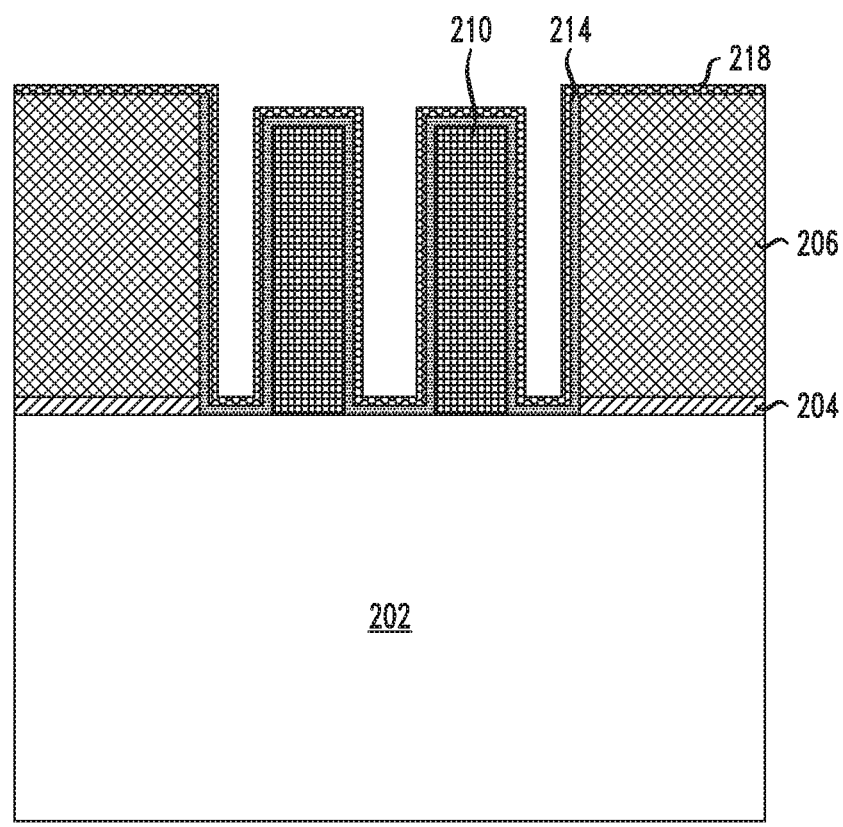
FIG. 13 is a schematic cross-sectional view of a semiconductor structure at a fifth-intermediate fabrication stage, according to another illustrative embodiment.

FIG. 13 illustrates a view of semiconductor structure 200 at a fifth-intermediate fabrication stage. During this stage, sacrificial material 216 is removed by conventional techniques, e.g., a gas phase HCL etch, and passivation layer 218 is deposited on the exposed surfaces of dielectric layer 208 and metal layer 214. Suitable material and deposition techniques for passivation layer 218 can be the same as those described above for passivation layer 116.

Figure 14:
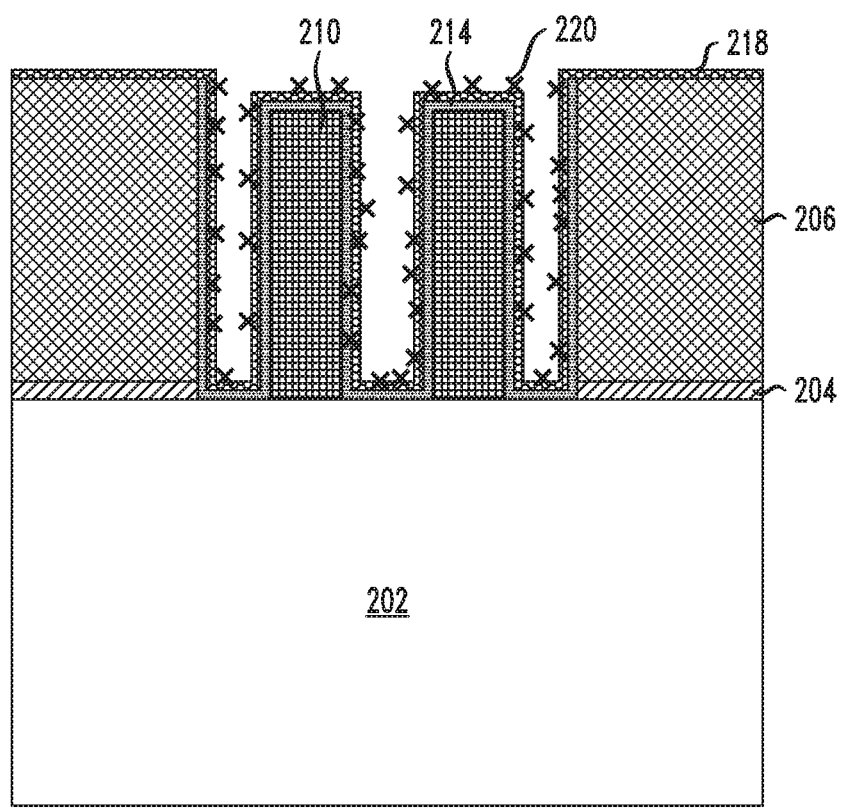
FIG. 14 is a schematic cross-sectional view of a semiconductor structure at a sixth-intermediate fabrication stage, according to another illustrative embodiment.
Figure 15:
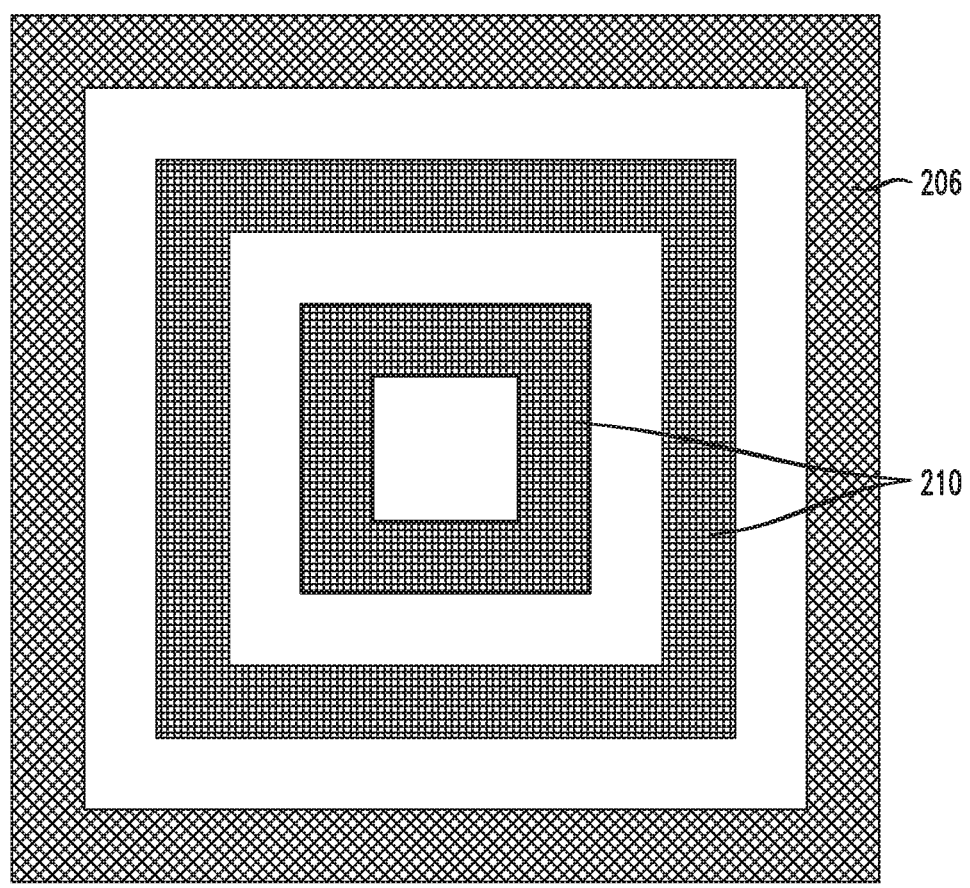
FIG. 15 is a top down view of the semiconductor structure of FIG. 14, in accordance with another illustrative embodiment.

FIG. 14 illustrates a view of semiconductor structure 200 at a sixth-intermediate fabrication stage. During this stage, an electrical charge 220 is introduced into passivation layer 218 by methods described above. The resulting ISFET will have enhanced sensitivity by increasing the passivation capacitance due to increase of surface area by forming multiple vertical rings inside the micro cell defined by $D_1$ using no hardmask. For example, FIG. 15 illustrates a top down view of the micro-well of semiconductor structure 200 of FIG. 13 after sacrificial layer 216 has been removed, such that semiconductor structure 200 has vertical rings for dielectric layer 206, and dielectric layers 210. In this example, sacrificial layer 216 is deposited for three times and the dielectric layer 210 is deposited twice to completely fill the micro-well before the sacrificial layer 216 is removed. The geometry of the vertical rings in the micro-well resulting from the selective etching of dielectric material can increase the total capacitor surface area as compared to other designs. In addition, this can enhance the sensitivity of the underlying ISFET by increasing capacitor surface area as compared to other designs.

Figure 16:
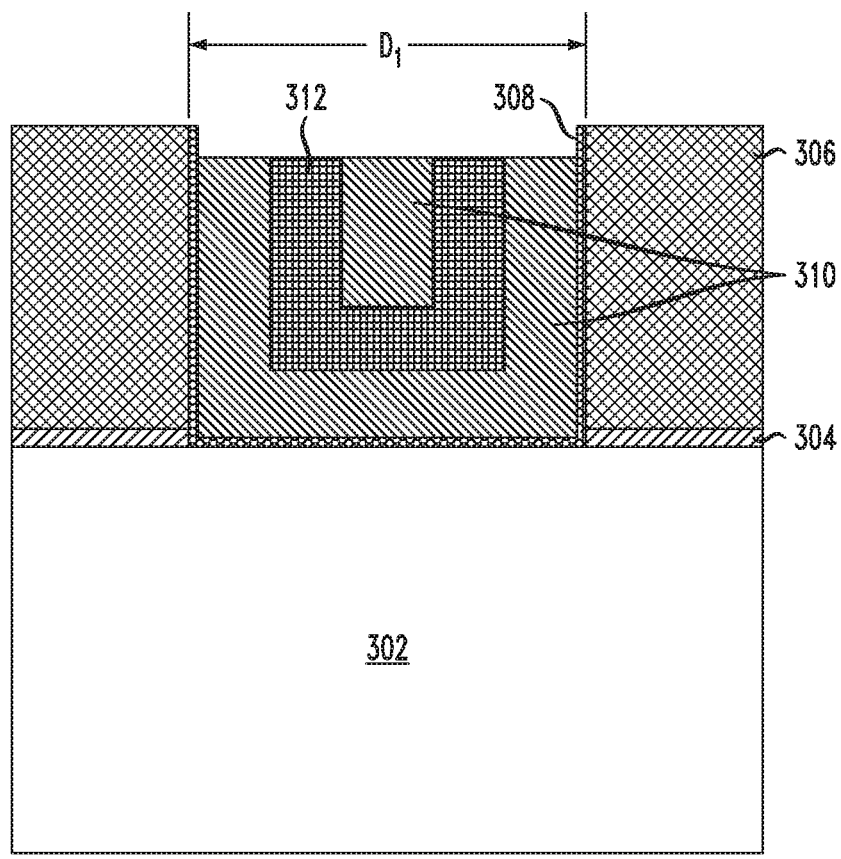
FIG. 16 is a schematic cross-sectional view of a semiconductor structure at a first-intermediate fabrication stage, according to an alternative illustrative embodiment.

Another illustrative embodiment for forming an ISFET will be described below with reference to FIGS. 16-20. Note that the same reference numeral (300) is used to denote the semiconductor structure through the various intermediate fabrication stages illustrated in FIGS. 16 through 20. Note also that the ISFET described herein can also be considered to be a semiconductor device and/or an integrated circuit, or some part thereof. FIG. 16 illustrates a cross sectional view of an ISFET at a first-intermediate fabrication stage. For the purpose of clarity, several fabrication steps leading up to the production of the ISFET as illustrated in FIG. 16 are omitted. In other words, the ISFET does not necessarily start out in the form illustrated in FIG. 16, but may develop into the illustrated structure over one or more well-known processing steps which are not illustrated but are well-known to those of ordinary skill in the art.

Referring to FIG. 16, a semiconductor structure 300 comprises a semiconductor base 302. In general, semiconductor base 302 can be the same as described above for semiconductor base 102. Semiconductor structure 300 further includes a passivation layer 304 disposed on a top surface of semiconductor base 302 and a dielectric layer 306 disposed on a top surface of passivation layer 304. Passivation layer 304 and dielectric layer 306 can be the same as those described above for passivation layer 104 and dielectric layer 106. A micro-well defined as $D_1$ is formed as described above.

Semiconductor structure 300 further includes metal layer 308 deposited on the exterior surface of the micro-well defined by $D_1$. Metal layer 308 can be the same material as those described above for metal layer 112. A conformal sacrificial layer 310 is then deposited. Sacrificial layer 310 can be the same material as those described above for sacrificial layer 208. Next, a conformal dielectric material 312 is deposited. Dielectric layer 312 can be the same material as those described above for passivation layer 210. Another sacrificial layer 310 is then deposited in and fills the opening in dielectric layer 312. In this embodiment, two sacrificial layer depositions and one dielectric layer deposition are used. However, other arrangements are contemplated herein. Next, a CMP process is performed to remove the multilayers on top of the metal layer 308 on top of the dielectric layer 306. The CMP process can also remove the horizontal portion of the metal layer 308 on top of dielectric layer 306. Alternatively, the CMP process can stop on top of the horizontal surface of the metal layer 308 on dielectric layer 306. The exposed metal layer 308 can be selectively removed by suitable methods known in art. Next, the top surface of the dielectric layer 310 and sacrificial layer 312 is recessed to below a top surface of dielectric layer 306. The top surface can be recessed using a selective directional removal technique that is selective to the dielectric layer 310 and sacrificial layer 312, for example, a wet or dry isotropic etch.

Figure 17:
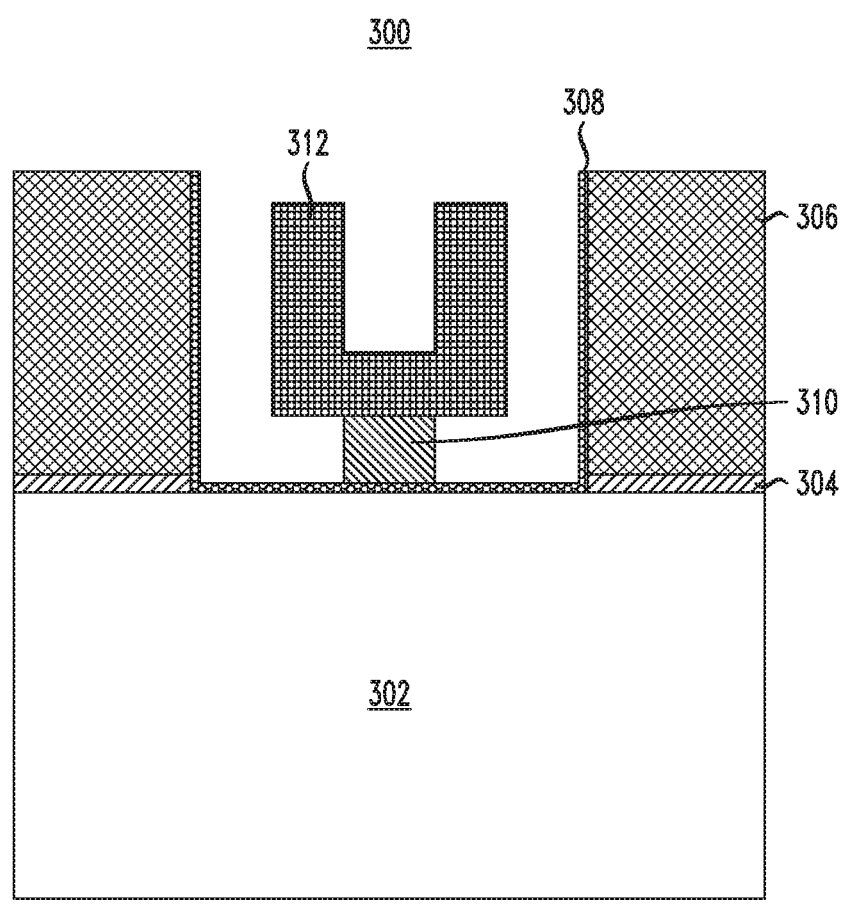
FIG. 17 is a schematic cross-sectional view of a semiconductor structure at a second-intermediate fabrication stage, according to an alternative illustrative embodiment.

FIG. 17 illustrates a view of semiconductor structure 300 at a second-intermediate fabrication stage. During this stage, a selective etch, e.g., isotropic etch, of the sacrificial layer 310 is carried out to leave a portion of the sacrificial layer 310 under dielectric layer 312 to support the dielectric layer 312 structure. In general, the remaining sacrificial layer 310 should have a thickness ranging from about 500 nm to about 1000 nm.

Figure 18:
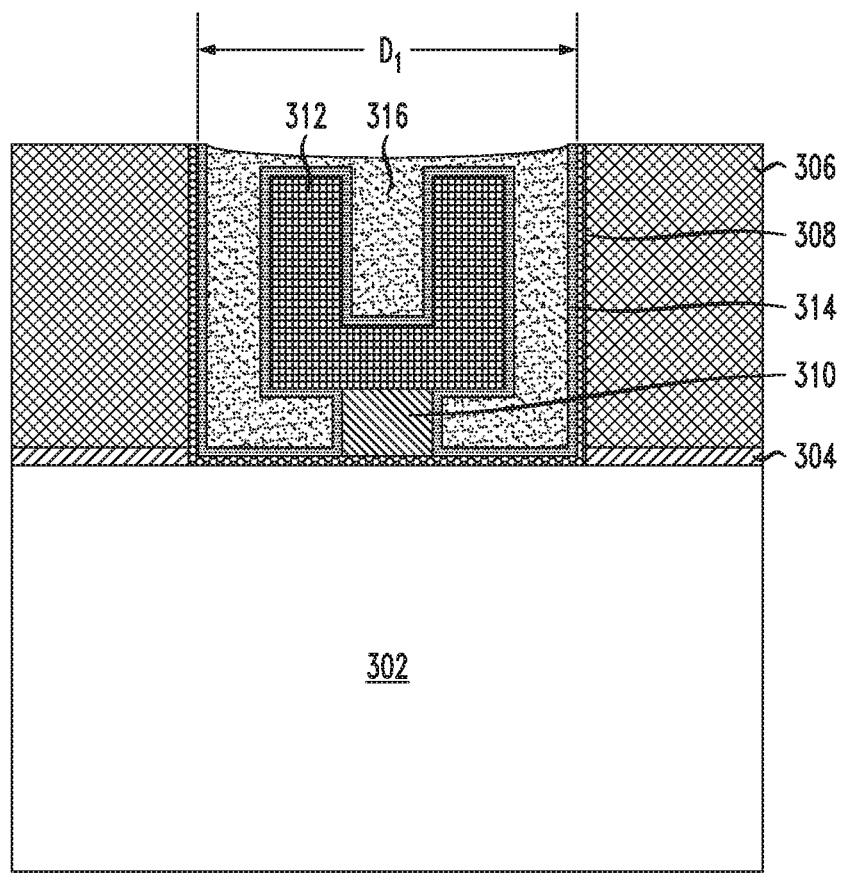
FIG. 18 is a schematic cross-sectional view of a semiconductor structure at a third-intermediate fabrication stage, according to an alternative illustrative embodiment.

FIG. 18 illustrates a cross-sectional view of semiconductor structure 300 at a third-intermediate fabrication stage. During this stage, metal layer 314 is deposited on the exposed surfaces of semiconductor structure 300. Suitable metallic material for metal layer 314 can be the same as those described above for metal layer 112. Metal layer 314 can be formed by a suitable deposition process, for example, ALD. Next, sacrificial material 316 is deposited in the micro-well defined by $D_1$ and over the top surface of semiconductor structure 300 including metal layer 314 (not shown). Suitable sacrificial material can be any of those described above for sacrificial material 114. Sacrificial material 316 can be deposited by any conventional deposition process such as CVD, PVD, PECVD, ALD, chemical solution deposition or other like processes. Sacrificial material 316 is then planarized by, for example, a planarization process such as a chemical mechanical planarization (CMP). Next, sacrificial material 316 is then recessed in the micro-well and exposes the top surface of metal layer 314 on the top surface of dielectric layer 306 (not shown). The exposed metal layer 314 on the top surface of dielectric layer 306 is then removed utilizing an isotropic etching process that selectivity removes the metal layer 314 and exposes the top surface of dielectric layer 306. The isotropic etch may be a wet or dry etch that is selective to the metal layer 314.

Figure 19:
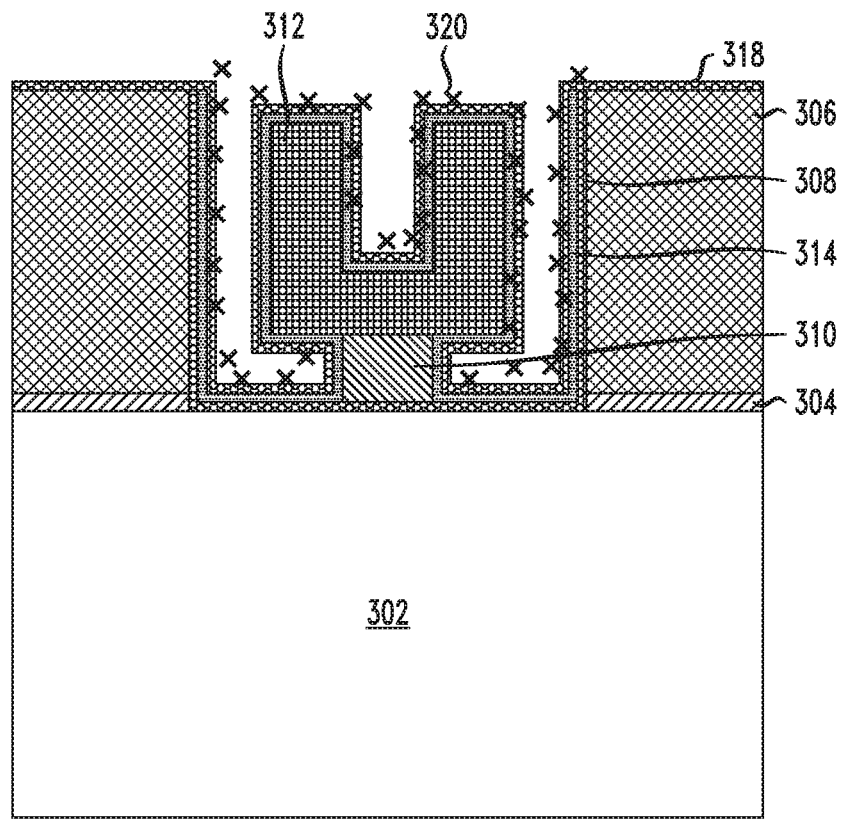
FIG. 19 is a schematic cross-sectional view of a semiconductor structure at a fourth-intermediate fabrication stage, according to an alternative illustrative embodiment.
Figure 20:
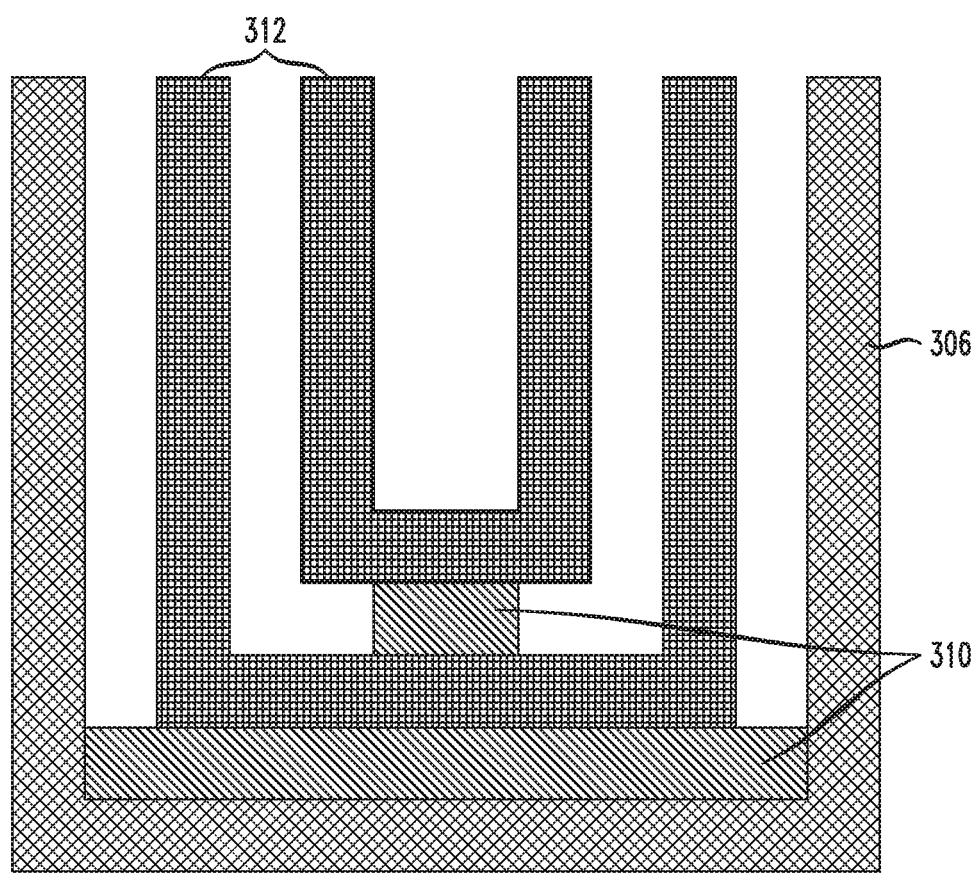
FIG. 20 is a top down view of the semiconductor structure of FIG. 19, in accordance with an alternative illustrative embodiment.

FIG. 19 illustrates a view of semiconductor structure 300 at a fourth-intermediate fabrication stage. During this stage, sacrificial material 316 is removed by conventional techniques as described above and passivation layer 318 is deposited on the exposed surfaces of dielectric layer 306 and metal layer 314. Suitable material and deposition techniques for passivation layer 318 can be the same as those described above for passivation layer 116. Next, an electrical charge 320 is introduced into passivation layer 318 by methods described above. The resulting ISFET will have enhanced sensitivity by increasing the passivation capacitance due to increase of surface area by forming multiple vertical rings with different heights inside the micro cell defined by $D_1$ using no hardmask. For example, FIG. 20 illustrates a cross-sectional view of the micro-well of semiconductor structure 300 of FIG. 17 after a portion of sacrificial layer 312 has been removed. The geometry of the vertical rings in the micro-well resulting from the selective etching of dielectric material can increase total capacitor surface area as compared to other designs. In addition, this can enhance the sensitivity of the underlying ISFET by increasing capacitor surface area as compared to other designs.

It is to be understood that the methods discussed herein for fabricating semiconductor structures can be incorporated within semiconductor processing flows for fabricating other types of semiconductor devices and integrated circuits with various analog and digital circuitry or mixed-signal circuitry. In particular, integrated circuit dies can be fabricated with various devices such as transistors, diodes, capacitors, inductors, etc. An integrated circuit in accordance with embodiments can be employed in applications, hardware, and/or electronic systems. Suitable hardware and systems for implementing embodiments of the invention may include, but are not limited to, personal computers, communication networks, electronic commerce systems, portable communications devices (e.g., cell phones), solid-state media storage devices, functional circuitry, etc. Systems and hardware incorporating such integrated circuits are considered part of the embodiments described herein.

Furthermore, various layers, regions, and/or structures described above may be implemented in integrated circuits (chips). The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Although illustrative embodiments have been described herein with reference to the accompanying drawings, it is to be understood that the invention is not limited to those precise embodiments, and that various other changes and modifications may be made by one skilled in art without departing from the scope or spirit of the invention.

What is claimed is:

1. A method for fabricating a semiconductor device comprising:
    depositing a first passivation layer on a semiconductor base;
    depositing a dielectric layer on the first passivation layer;
    depositing a hardmask on the dielectric layer;
    patterning and etching an opening into the hardmask, the dielectric layer, and the first passivation layer which exposes a top surface of the semiconductor base and forms a plurality of pillars in the opening, wherein a top surface of the plurality of pillars is below a top surface of the hardmask on the dielectric layer defining a width of the opening;
    depositing a metal layer on the exterior surfaces of the dielectric layer, the plurality of pillars and the exposed top surface of the semiconductor base in the opening and over the top surface of the hardmask on the dielectric layer defining the width of the opening;
    depositing a sacrificial layer in the opening;
    removing the metal layer disposed on the top surface of the hardmask on the dielectric layer;

depositing a second passivation layer on the metal layer and the top surface of the hardmask on the dielectric layer; and forming an electrical charge in the second passivation layer.

2. The method of claim 1, wherein the semiconductor base comprises a complementary metal oxide semiconductor integrated circuit.

3. The method of claim 1, wherein the step of patterning and etching the opening into the hardmask, the dielectric layer and the first passivation layer comprises:

etching the hardmask, the dielectric layer and the first passivation layer to form the opening and the plurality of pillars therein which exposes a top surface of the first passivation layer; and etching the exposed first passivation layer to expose the top surface of the semiconductor base.

4. The method of claim 1, wherein the first passivation layer comprises silicon nitride (SiN).

5. The method of claim 1, wherein the metal layer comprises a metal selected from the group consisting of tungsten, titanium, tantalum, ruthenium, zirconium, cobalt, copper, aluminum, lead, platinum, tin, silver, and gold.

6. The method of claim 5, wherein the sacrificial layer comprises one of an amorphous silicon and an amorphous silicon germanium alloy (aSiGe).

7. The method of claim 6, wherein the second passivation layer comprises one of SiN, $Al_2O_3$, and $Ta_2O_5$.

8. The method of claim 1, wherein the step of forming the electrical charge in the second passivation layer comprises contacting the second passivation layer with a solution comprising an anion or a cation.

\* \* \* \* \*